United States Patent [19]

Levine et al.

[11] Patent Number: 4,700,715
[45] Date of Patent: Oct. 20, 1987

[54] DEVICE FOR DETECTING NOCTURNAL PENILE ERECTIONS

[76] Inventors: Robert A. Levine, 31 Pilgrim La., Guilford, Conn. 06437; Stephen C. Wardlaw, 191 North Cove Rd., Old Saybrook, Conn. 06475

[21] Appl. No.: 324,073

[22] Filed: Nov. 23, 1981

[51] Int. Cl.$^4$ ................................................ A61B 5/10
[52] U.S. Cl. ...................................... 128/774; 73/787
[58] Field of Search ............ 33/2 R, 2 A, 2 H, 137 R, 33/174 D, 178 R; 73/762, 787, 862.53, 212, DIG. 34; 128/79, 132 R, 283, 294, 295, 686, 687, 690, 691, 774, 782; 604/346–347, 349–352

[56] References Cited

U.S. PATENT DOCUMENTS

| | | | |
|---|---|---|---|
| 3,416,522 | 12/1968 | Yeremian | 128/132 R |
| 3,613,679 | 10/1971 | Bijou | 116/114 |
| 3,669,096 | 6/1972 | Hurwitz | 128/686 |
| 4,018,085 | 4/1977 | Alley, Jr. et al. | 73/787 |
| 4,103,678 | 8/1978 | Karacan et al. | 128/774 |
| 4,239,044 | 12/1980 | Pavlinch | 128/295 |
| 4,292,851 | 10/1981 | Brewer | 73/762 |

FOREIGN PATENT DOCUMENTS 1918876 10/1970 Fed. Rep. of Germany ...... 128/283

OTHER PUBLICATIONS

Barry et al, "Nocturnal Penile Tumescence Monitoring with Stamps", Urology, Feb., 1980, pp. 171–172.

Primary Examiner—Kyle L. Howell
Assistant Examiner—Francis J. Jaworski
Attorney, Agent, or Firm—William W. Jones

[57] ABSTRACT

A device which is circumferentially affixed to a flaccid penis about the proximal portion of the shaft thereof prior to retiring at night. The device is in the form of a band of material which includes an expandable portion which will not retract once expanded. In the event of a nocturnal erection, the device will expand in response to circumferential enlargement of the penis which occurs during the erection. The expanded device is retrieved upon arising in the morning and is dispatched to one's physician for analysis.

16 Claims, 4 Drawing Figures

DEVICE FOR DETECTING NOCTURNAL PENILE ERECTIONS

This invention relates to a device which is used to detect nocturnal penile erections of which the user would be otherwise unaware. More particularly, the device of this invention is useful for detecting and determining quantitative data regarding one's ability to achieve an erection.

Historically impotence has been accepted as a condition for which there was no ready cure, but recently many significant advances have been made in its treatment. Of paramount importance in the proper management of any disease, including impotence, is the accurate evaluation of its underlying cause. In the past, in the case of male impotence, the identification of the underlying cause or causes has been difficult to establish except in a minority of cases. Recently, however, a greater understanding of the basic psychophysiologic process involved has been achieved so that a relatively rapid and sure diagnosis of the various causes of impotence can be made by a physician. The basis of this new approach is the realization that organic causes of impotence can be distinguished from psychological causes by the employment of a relatively simple test, which involves the evaluation of Nocturnal Penile Tumesence (NPT).

All males with intact physical processes exhibit NPT, or nocturnal erections, during the REM phase of sleep. Physiologic studies have determined that the presence of such nocturnal erections is proof of the physical ability to achieve an erection, so that, if the nocturnal erection is present then the cause of the impotence is psychological. The difficulty is that the patient is asleep during the achievement of such nocturnal erections and thus may not be aware of their occurrence. In order to record such nocturnal erections, relatively complex apparatus has been developed, such as penis plethysmographs. Although mechanically effective, such apparatus is restricted in its use to specialists due to its complexity and high cost. In addition, these devices require that the patient be wired to the device so that the diagnostic readings can be taken while the patient is asleep.

The device of this invention is an inexpensive disposable device which can be used by the patient in the privacy of his own home to detect and measure certain data relating to nocturnal erections. Basically, the device comprises a band of material, preferably sheetlike, which is wrapped around the circumference of the proximal portion of the shaft of the flaccid penis just prior to retiring at night. The material from which the device is constructed is preferably a prepared metallic foil or some other material which can elongate under stress and will remain elongated upon removal of the stress. At least a portion of the band is expandable in the long direction of the band, and, once expanded, will not retract back to its initial dimension. The increase in the girth of the penis which occurs during the change from the flaccid condition to the erect condition will cause the expansion of the expandable portion of the band, and when the penis returns to its flaccid condition after the erection, the band will remain expanded. The expandable portion of the band can be formed from an appropriately slitted metallic foil material, such as copper or aluminum foil, or from some other expandable material without memory. The band is also adapted to measure and record the circumference of the flaccid penis so that a quantitative analysis of the ability to achieve an erection may be made y comparing the flaccid circumference with the erect circumference.

It is, therefore, an object of this invention to provide a device for detecting the occurrence of nocturnal erections in apparently impotent males.

It is a further object of this invention to provide a device of the character described which is inexpensive, simple to use, and disposable after analysis.

It is an additional object of this invention to provide a device of the character described which is in the form of a band of material adapted to be wrapped about the circumference of the penile shaft when flaccid, and at least a portion of which is expansible, and not retractable once expanded, to detect expansion of the circumference of the penile shaft during nocturnal erection.

It is yet another object of this invention to provide a device of the character described which is adapted to measure and record the circumferential dimension of the shaft of the penis while in the flaccid state to provide data enabling quantitative analysis of the erection to be made.

These and other objects and advantages of the invention will become more readily apparent from the following detailed description of a preferred embodiment thereof taken in conjunction with the accompanying drawings, in which.

Figure 1:
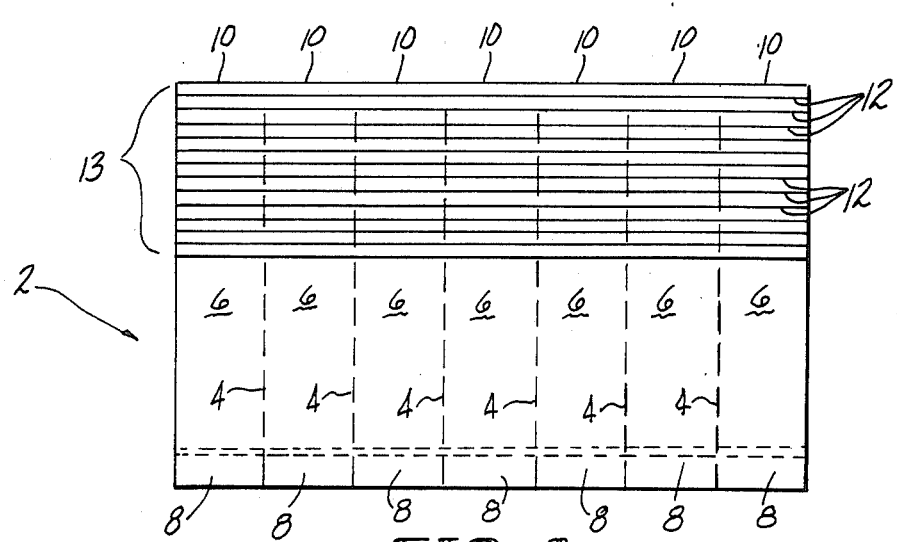
FIG. 1 is a plan view of a sheet of stock material from which individual devices of this invention are cut and produced.

Referring now to the drawings, there is shown in FIG. 1 a sheet of stock material, denoted generally by the numeral 2, from which individual devices formed in accordance with this invention are made. The stock sheet material, in the embodiment shown, is preferably metal foil. The sheet 2 is cut along parallel lines 4 to form a plurality of the individual devices 6, which, it will be noted, take the form of bands or strips. The individual strips 6 are provided with a coating of adhesive on the bottom side of a tabbed end 8, and are preferably also provided with a coating of adhesive on the top side of the opposite end 10. The top side of the strips 6 at the opposite end 10 is provided with a plurality of parallel reference lines 12 which form a measuring zone 13 which extends a predetermined distance along the elongated dimension of the strip 6. Preferably, the adhesive coated onto the top side of the end 10 extends over the entire measuring zone 13. The adhesives preferred for use are adhesives such as rubber based contact adhesives which adhere only to a similar adhesive coating, and to nothing else. Thus the device will not stick to the skin, pubic hair, clothing, or the like when applied to the penis.

Figure 2:
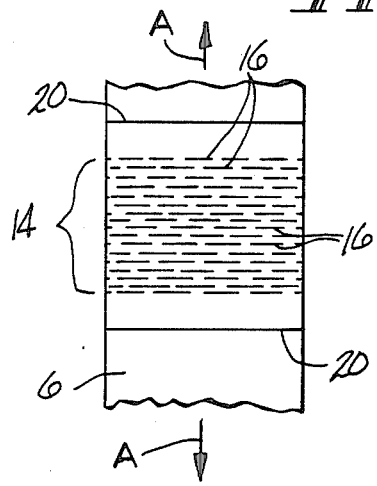
FIG. 2 is a plan view of a preferred embodiment of the expansion portion of the device shown prior to expansion thereof.
Figure 3:
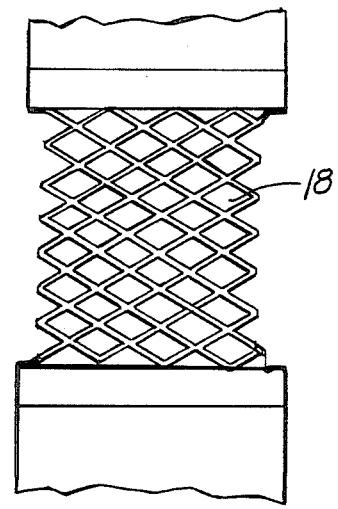
FIG. 3 is a plan view similar to FIG. 2 but showing the expansion portion of the device after expansion thereof has occurred.
Figure 4:
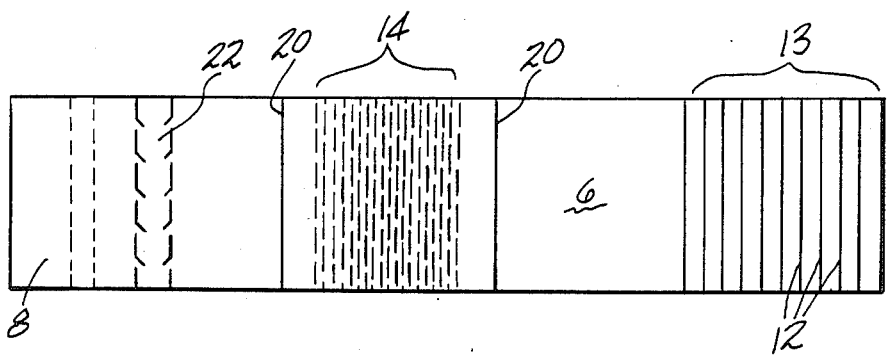
FIG. 4 is a plan view of a preferred embodiment of a completed device formed in accordance with this invention.

Between the measuring zone 13 and the tab 8, there is positioned the expansion zone which is shown in detail in FIG. 2. In the embodiment shown, the strip 6 is made of metallic foil, and the expansion zone 14 is formed by forming a grid pattern of through cuts 16 in the foil. The cuts 16 will open up into a diamond lattice structure 18, as shown in FIG. 3, when the strip 6 is pulled in opposite directions, indicated by arrows A, at the same time. Reference lines 20 are formed on the strip 6 on both side of the expansion zone 14. Referring now to FIG. 4, a complete device is shown, which includes the foil strip 6, the adhesive tab 8, the measuring zone 13, and the expansion zone 14. The device also includes a rupturable tear strip 22 for removing the device from the penis upon awakening.

The manner in which the device is used will now be set forth in detail. When the patient is about to retire to bed for the evening, he wraps the strip 6 about the proximal portion of the penile shaft while the penis is flaccid. To secure the strip 6 in place, the adhesive coated tab 8 is pressed onto the adhesive coated measuring zone 13 to relatively snugly secure the strip 6 about the flaccid penis. The particular reference line 12 at which the free end of the tab 8 lies will measure and record the circumference of the flaccid penis. The patient then retires to bed. During the night, the strip 6 is relatively snugly wrapped about the shaft of the penis, so that if and when an erection occurs, the circumference of the penile shaft will increase. As the penile circumference increases, the expansion zone will expand from the form shown in FIG. 2 to the form shown in FIG. 3 due to the fact that the opposite ends of the expansion zone 14 will be pulled away from each other by the expanding penis. When the erection subsides, the expansion zone 14 will remain in the expanded state shown in FIG. 3 due to its inability to retract. Upon awakening in the morning, the strip 6 is removed from the penis by tearing away the tear strip 22 thereby laterally severing the strip 6. Removal of the tear strip 22 leaves the tab 8 in place on the measuring zone 13 thereby preserving the flaccid penis circumference measurement for recording by the physician. The removed strip 6 is then returned to the physician for analysis.

It will be noted that only a portion of the strip 6 is expandable, and the remainder of the strip 6 is non-expandable. With this arrangement, the entire extent of circumferential penile expansion is reflected by the expandable portion of the strip. In this manner, more accurate measurement of the penile circumferential expansion is made possible than if the entire strip were made expandable. Preferably, the expandable portion of the strip constitutes less than half of the longitudinal extent of the strip, and most preferably, it constitutes about one-third of the longitudinal extent of the strip. When the physician receives the used strip 6, the flaccid penis circumference is noted, and the distance between the reference lines 20 is measured. This measurement is compared to the known distance between the reference lines 20 in an unused strip, which is standardized. The difference constitutes the increase in circumference of the penis which was achieved during the erection. By comparing the flaccid penis circumference with the erected penis circumference, the magnitude of the erection achieved can be determined. In this manner, the degree of impotency can be diagnosed, and a plan of treatment can be formulated. Naturally, if the strip indicates that no erection occurred during sleep, then the cause of the impotency can be diagnosed as physiological, and a plan of treatment can be formulated and further tests conducted.

As an alternative to the use of a tab and tear strip for preserving the flaccid penile circumference measurement, the strip can employ colored adhesives that leave behind a mark when the strip is peeled back to remove it from the penis. In this mode, the tear strip is eliminated and the color residue left behind indicates the flaccid penile circumference measurement.

In order to protect the patient from any possible irritation from the expandable zone, the strip, or at least the expandable portion thereof, can be sheathed in a soft, relatively elastic, fabric, which may be felted onto the strip.

It will be readily appreciated that the device of this invention is relatively inexpensive to manufacture, and is of simple, yet dependable, construction, when compared to presently available alternatives. The principle employed relates to the use of a limited portion of the strip being expandable when stressed, and not retractable when relieved of stress, with the remainder of the strip being non-expandable when exposed to penile erection pressure. The use of the limited expansion portion ensures that substantially the entire extent of penile expansion which occurs circumferentially will be sensed by the limited expansion portion of the strip so that the error factor is substantially reduced.

Since many changes and variations of the disclosed embodiment of the invention may be made without departing from the inventive concept it is not intended to limit the invention otherwise than as required by the appended claims.

What is claimed is:

1. A device for detecting nocturnal penile erections, said device comprising: an elongated band of sheetlike material adapted to snugly encircle a flaccid penile shaft; said band having one end portion provided with a plurality of spaced indicia markings with the other end of said band being adapted to overlie said one end portion when said band encircles the flaccid penile shaft to provide an indication of the circumferential dimension of the flaccid penile shaft; adhesive means on said band to secure said ends of said band in overlying relationship; and means providing a dimensionally restricted expansion portion medially on said band, said expansion portion being operable to expand in the direction of elongation of said band during transition of the penis from the flaccid to the erection state to increase the dimension of said band in said direction of elongation, and said expansion portion comprising a substantially non-resilient material whereby the increased direction of elongation dimension is retained during retransition of the penis from the erection to the flaccid state.

2. The device of claim 1, wherein said expansion portion occuppies less than about fifty percent of the length of said band.

3. The device of claim 1, wherein said expansion portion occuppies approximately one-third of the length of said band.

4. The device of claim 1, further comprising reference markings disposed on each side of said expansion portion to provide means for accurately measuring the extent of expansion of said expansion portion.

5. The device of claim 1, further comprising a rupturable tear strip traversing the narrow dimension of said band to provide means for releasing said band from engagement with the penis without disrupting said overlying relationship of said ends of said band.

6. The device of claim 1, wherein said adhesive means is differentially colored to form a residual colored indication of the extent of overlap of said ends of said band after said ends of said band are peeled away from each other to release said band from encirclement of the penis.

7. The device of claim 1, wherein said band is formed from metallic foil.

8. The device of claim 7, wherein said expansion portion comprising a plurality of transverse slits in said foil band patterned to form an expanded diamond grid when subjected to penile pressure during transition of the penis from the flaccid to the erection state.

9. The device of claim 8, wherein at least said expansion portion is provided with a protective covering to prevent irritation of the penis.

10. The device of claim 1, wherein said adhesive means is a contact cement.

11. A device for detecting nocturnal penile erections said device comprising: an elongated band of metallic foil adapted to snugly encircle a flaccid penile shaft; means for securing opposite ends of said band together to secure said band about the penile shaft; and an expansion portion on said band comprising a plurality of transverse slits in said foil patterned to form an expanded diamond grid when subjected to penile pressure during transition of the penis from the flaccid to the erection state which expanded diamond grid is retained during retransition of the penis from the erection to the flacid state.

12. The device of claim 11, further comprising reference indicia disposed on each side of said expansion portion to provide means for accurately measuring the extent of expansion of said expansion portion.

13. The device of claim 11, wherein at least said expansion portion is provided with a protective covering to prevent irritation of the penis.

14. The device of claim 11, wherein one end portion of said band is provided with a plurality of indicia operative to provide an indication of the flaccid penile circumferential dimension when said one end portion is overlapped by the other end of said band when said band is secured to the penis.

15. The device of claim 14, wherein said means for securing comprises colored adhesive operable to form a residual colored indication on said plurality of indicia after said ends of said band are peeled away from each other to release said band from encirclement of the penis.

16. The device of claim 14, further comprising a rupturable tear strip traversing the narrow dimension of said band to provide means for releasing said band from engagement with the penis without disrupting the overlapping relationship of said ends of said band.

* * * * *